(12) United States Patent
Eldin

(10) Patent No.: US 6,639,026 B2
(45) Date of Patent: Oct. 28, 2003

(54) METHODS AND COMPOSITIONS FOR INHIBITING POLYMERIZATION OF VINYL MONOMERS

(75) Inventor: Sherif Eldin, Houston, TX (US)

(73) Assignee: GE Betz, Inc., Trevose, PA (US)

( * ) Notice: Subject to any disclaimer, the term of this patent is extended or adjusted under 35 U.S.C. 154(b) by 144 days.

(21) Appl. No.: 09/862,406

(22) Filed: May 22, 2001

(65) Prior Publication Data

US 2003/0008981 A1 Jan. 9, 2003

(51) Int. Cl.$^7$ .................................................. C08F 2/38
(52) U.S. Cl. ........................... 526/82; 526/83; 526/84; 526/348; 526/348.2; 526/348.3; 526/348.6; 526/335
(58) Field of Search ............................ 526/82, 83, 84, 526/348, 348.2, 348.3, 348.6, 335

(56) References Cited

U.S. PATENT DOCUMENTS

| | | | |
|---|---|---|---|
| 3,148,225 A | 9/1964 | Albert | 260/669 |
| 3,342,723 A | 9/1967 | Godar | 208/48 |
| 3,488,338 A | 1/1970 | Bailey et al. | 206/92.3 |
| 3,733,326 A | 5/1973 | Murayama et al. | 260/290 |
| 3,747,988 A | 7/1973 | Bailey | 203/8 |
| 4,456,526 A | 6/1984 | Miller et al. | 208/48 |
| 4,670,131 A | 6/1987 | Ferrell | 208/48 AA |
| 4,720,566 A | 1/1988 | Martin | 558/306 |
| 5,254,760 A | 10/1993 | Winter et al. | 585/5 |
| 5,258,138 A | 11/1993 | Gatechair et al. | 252/403 |
| 5,290,888 A | 3/1994 | Gatechair et al. | 526/83 |
| 5,416,258 A | 5/1995 | Arhancet et al. | 585/3 |
| 5,510,547 A | 4/1996 | Arhancet et al. | 585/5 |
| 5,711,767 A | 1/1998 | Gande et al. | 44/423 |
| 5,728,872 A | 3/1998 | Riemenschneider | 562/598 |
| 5,888,356 A | 3/1999 | Keil et al. | 203/8 |
| 6,020,435 A * | 2/2000 | Blankenship et al. | 525/256 |
| 6,200,461 B1 * | 3/2001 | Eldin | 208/48 |

FOREIGN PATENT DOCUMENTS

| | | | |
|---|---|---|---|
| EP | 0 467 849 B1 | 4/1995 | C07C/69/54 |
| EP | 0 908 505 A1 | 4/1999 | C10G/9/00 |
| WO | 98/02400 | 1/1998 | C07B/63/04 |
| WO | 98/58038 | 12/1998 | C09K/15/30 |
| WO | 98/59016 | 12/1998 | C09K/15/24 |
| WO | 99/07664 | 2/1999 | C07C/67/62 |
| WO | 99/55797 | 11/1999 | C09K/15/18 |
| WO | WO 0036052 * | 6/2000 | |
| WO | 00/36052 | 6/2000 | C09K/15/20 |

OTHER PUBLICATIONS

CN 86103840 Su, Bincheng (Jinxi Chem. Eng. Ins.) (Abstract).

* cited by examiner

Primary Examiner—David W. Wu
Assistant Examiner—William Cheung
(74) Attorney, Agent, or Firm—Steven D. Boyd

(57) ABSTRACT

Methods and compositions for inhibiting the polymerization of vinyl monomers are disclosed. Combinations of aminophenol compounds and nitroxyl radical compounds are effective at inhibiting vinyl monomer polymerization under both processing and storage conditions.

13 Claims, 2 Drawing Sheets

METHODS AND COMPOSITIONS FOR INHIBITING POLYMERIZATION OF VINYL MONOMERS

FIELD OF THE INVENTION

The present invention provides for methods and compositions for inhibiting the polymerization of vinyl monomers, such as olefins and diolefins.

BACKGROUND OF THE INVENTION

Common industrial methods for producing vinyl monomers include a variety of purification processes such as distillation to remove impurities. Purification operations are often carried out at elevated temperatures and this can increase the rate of undesired polymerization. Polymerization, such as thermal polymerization, during the monomer purification process, results not only in loss of desired monomer end-product, but also in production efficiency caused by polymer formation and deposition on process equipment. Undesirable polymerization causes monomer loss, and may cause operational problems such as increase in fluid viscosity, temperature, restricted flow in pipelines, and block filters. In heat requiring operations, such deposition adversely affects heat transfer efficiency.

Typically the monomers are stabilized with the addition of substances which will act as inhibitors or retarders of polymerization.

Certain vinyl monomers such as the diolefins butadiene and isoprene will polymerize when left in storage tanks and during transportation at temperatures as low as room temperature. This polymerization is initiated by reaction of the diolefin monomer with oxygen present in the monomer containing system. This reaction will form peroxides and free radical species which will perpetuate the reaction with the diolefin monomer.

Various approaches have been attempted with regard to this problem of polymerization. U.S. Pat. No. 3,148,225 teaches that N,N-dialkylhydroxylamines will inhibit the polymerization of popcorn polymer formation in olefin monomer recovery systems. In comparative studies, p-aminophenol was less effective than the hydroxylamines at inhibiting popcorn polymer formation. U.S. Pat. No. 6,200,461 teaches the use of combinations of aminophenols with dialkylhydroxylamines or phenylenediamines. U.S. Pat. No. 3,342,723 tests p- and o-aminophenols for inhibiting fouling of hydrocarbon liquids. These compounds proved effective at inhibiting the formation and adhesion of coke-like deposits during refinery operations.

U.S. Pat. No. 5,510,547 teaches that a combination of a phenylenediamine compound and a hydroxylamine compound is effective at inhibiting the polymerization of vinyl aromatic monomers during processing conditions. U.S. Pat. No. 4,720,566 teaches that a combination of a hydroxylamine and a phenylenediamine compound is effective at inhibiting the polymerization of acrylonitrile during its production.

The use of 2,2,6,6-teteramethylpiperidine-N-oxyl (nitroxyl radical) based stable free radicals for controlling free radical polymerization of reactive monomers is well established in literature. U.S. Pat. No. 3,747,988 teaches its use for controlling acrylonitrile polymerization, U.S. Pat. No. 3,733,326 teaches its use for stabilizing vinyl monomers, U.S. Pat. No. 3,488,338 teaches its use for short-stopping the polymerization of chloroprene, U.S. Pat. No. 4,670,131 claims the use of nitroxyl radicals in the range of 20 ppb to 700 ppm for controlling fouling of vinyl monomers.

TEMPO-based nitroxyl radicals are relatively expensive. Synergistic combinations of nitroxyl radicals with other compounds have benefits (economic and technical) and there are a number of patents that teach these types of combinations. Examples are; U.S. Pat. No. 5,711,767 for the use of nitroxyl radical molecules with phenylenediamines to prevent gum formation in gasoline, U.S. Pat. No. 5,888,356 for the use of nitroxyl radicals with nitrosophenols for stabilizing vinyl monomers, U.S. Pat. No. 5,728,872 for the use of nitroxyl radicals with dihetero-substituted benzene for stabilizing acrylic acid, and U.S. Pat. No. 5,254,760 for the use of nitroxyl radicals with aromatic nitro compounds for stabilizing vinyl aromatic monomers.

BRIEF SUMMARY OF THE INVENTION

The present invention is directed to methods and compositions for inhibiting the polymerization of vinyl monomers. Undesired polymerization of vinyl monomers during processing (such as purification via distillation), storage and/or transportation adversely impacts production efficiency. For example, vinyl monomers such as olefins, diolefins, butadiene and isoprene can polymerize during storage and/or transportation at temperatures as low as room temperature. The present invention is directed toward the discovery that a composition comprising a combination of at least one aminophenol compound and a nitroxyl radical compound can inhibit undesired polymerization of vinyl monomers.

DETAILED DESCRIPTION OF THE INVENTION

Figure 1:
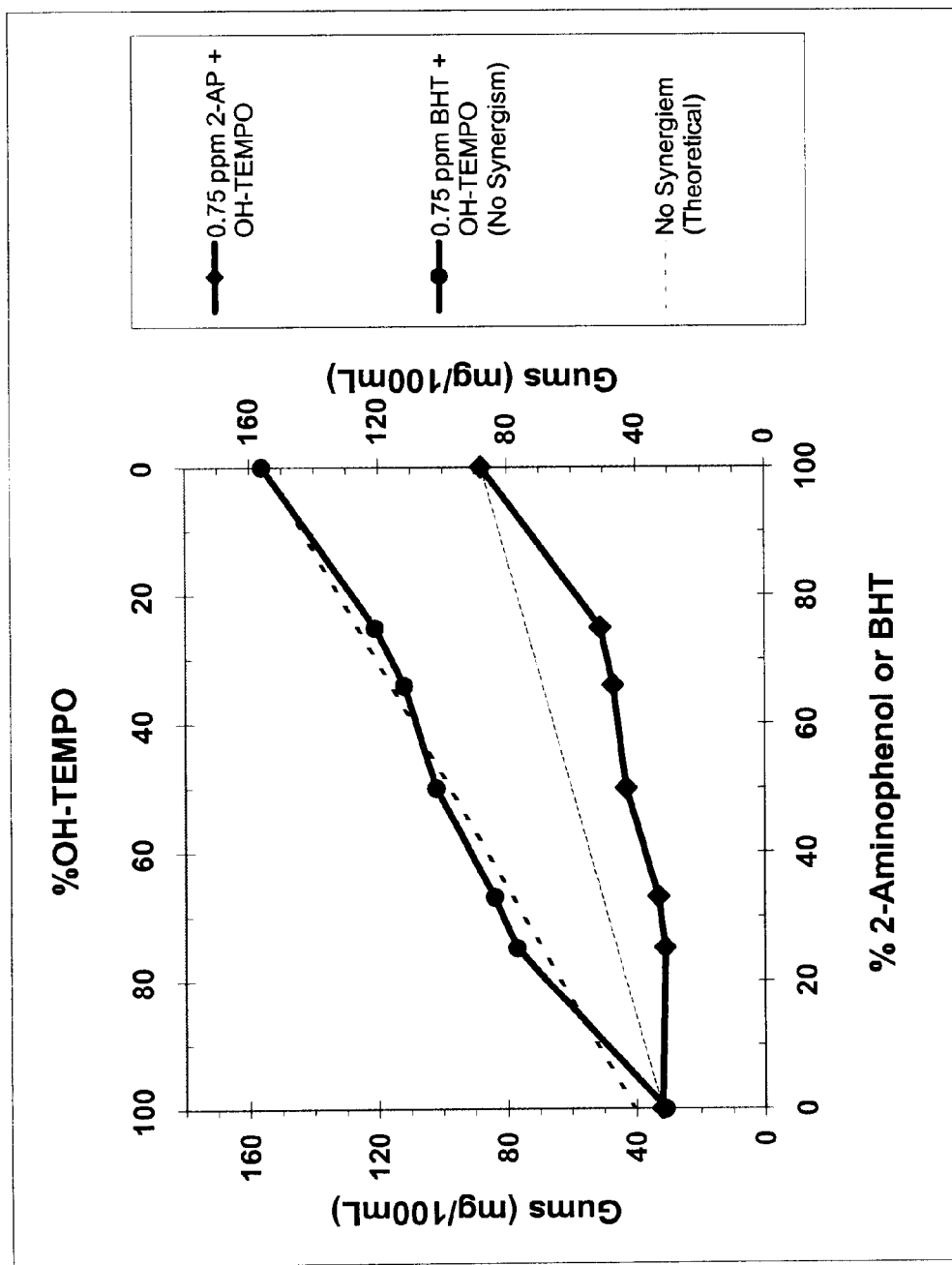
FIG. 1 is a graph of gum formation versus composition component ratio for components tested and results reported in Tables I and III below.

The present invention provides for methods and compositions for inhibiting the polymerization of vinyl monomers comprising an effective inhibiting composition which comprises (A) at least one aminophenol compound (B) at least one nitroxyl radical compound.

The aminophenol compounds may be selected from the compounds given by the generalized formula:

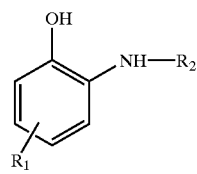

Where $R_1$ is selected from hydrogen, a $C_1$–$C_{20}$ alkyl group, aryl group, or OR', with R' being a H, an alkyl or an aryl group. $R_2$ is selected from an alkyl, a phenyl group, or OR', with R' having the same meaning as before.

Non-exclusive examples of such compounds are 2-aminophenol, 3-hydroxy-2-aminophenol, 2-amino-naphthalen-1-ol, 3-amino-naphthalen-2-ol, 1-amino-naphthalen-2-ol, 2-amino-tert-butyl-phenol, and 2-amino-4-methyl-phenol. Exemplary nitroxyl radical compounds include, but are not limited to derivatives of dialkyl nitroxyl radicals and 1-oxyl-2,2,6,6-tetraalkylpiperidine compounds such as 1-oxyl-2,2,6,6-tetramethylpiperidine, 1-oxyl-2,2,6,6-tetramethylpiperidin-4-ol (OH-TEMPO), 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, bis(1-oxyl-2,2,6,6-tetramethylpiperidin-4-yl)n-butylmalonate, bis(1-oxyl-2,2,6,6-tetramethylpiperidin-4-yl)phthalate, bis(1-oxyl-2,2,6,6-tetramethylpiperidin-4-yl)isophthalate, bis(1-oxyl-2,2,6,6-tetramethylpiperidin-4-yl)terephthalate, bis(1-oxyl-2,2,6,6-tetramethylpiperidin-4-yl)hexahydroterephthalate, N,N'-bis(1-oxyl-2,2,6,6-tetramethylpiperidin-4-yl)adipamide, N-1-oxyl-2,2,6,6-tetramethylpiperidin-4-yl-dodecylsuccinimide, 1-oxyl-4-methoxy-2,2,6,6-tetramethylpiperidine, 1-oxyl-4-amino-2,2,6,6-tetramethylpiperidine and 1-oxyl-4-acetamino-2,2,6,6-tetramethylpiperidine.

The monomers are characterized as polymerizable vinyl monomers and include olefins and diolefins. The olefins contain about 2 to about 20 carbon atoms, preferably 2 to 8 carbon atoms and the diolefins are conjugated and contain about 4 to about 20 carbon atoms with 4 to 6 carbon atoms preferred. Examples of these compounds include ethylene dichloride, vinyledene chloride, ethylene glycol, aromatics from ethylene plants and pyrolysis gasoline, butadiene, isoprene, cyclopentadiene, vinylacetate, acrylonitile, methacrylic acid, and methylmethacrylate.

The inhibitor compositions of the present invention are effective at inhibiting the polymerization of vinyl monomers during both storage and processing conditions. Storage conditions also include transportation of the monomers. These conditions will usually have oxygen present and can be at elevated temperatures of up to 100° C. The processing conditions are usually distillation and purification processes and are run at elevated temperatures of 50° and 150° C. where oxygen can be present or absent.

For purposes of the present invention, the term "effective amount for the purpose" is that amount of inhibitor compositions necessary to inhibit polymerization of the vinyl monomers. This amount will vary according to the conditions under which the monomers are subjected during the storage and/or handling thereof. During processing, for example, high temperatures and higher monomers contamination will require larger amounts of the inhibitor compositions.

Preferably, the total amount of the inhibitor compositions added to the vinyl monomer will range from about 1 part to about 10,000 parts per million parts of monomer. More preferably, the inhibitor compositions are added at a range of about 1 part to about 100 parts per million parts monomer.

The weight ratio of aminophenol compound to nitroxyl radical compound in the inhibitor composition can generally vary from about 1:9 to about 9:1.

Accordingly, it is possible to produce a more effective vinyl monomer polymerization inhibition treatment than is obtainable by the use of one ingredient alone when measured at comparable treatment levels. This enhanced activity will allow for the concentration of each of these ingredients to be lowered and the total quantity of polymerization inhibitor particularly at higher processing temperatures may be reduced.

The inhibitor compositions of the present invention may be added to the vinyl monomers as either a dispersion or as a solution using a suitable liquid carrier or solvent. Any solvent that is compatible with the individual ingredients and with the monomer may be employed. The compositions may be introduced by any conventional method at any point in the processing system.

The inhibitor compositions may be added to the vinyl monomers by any conventional method, either as individual components or as a combination of components. It is preferred that the ingredients be added to the monomer as a single treatment.

This invention will now be further described with reference to a number of specific examples which are to be regarded solely as illustrative and not as restricting the scope of the invention.

EXAMPLES

20% uninhibited isoprene in heptane was placed in a pressure vessel. This mixture was then purged once with nitrogen before placing it under 100-psi nitrogen. The pressure vessel was then placed in a 100° C. water bath for 4 hours allowing polymerization of the diolefin. The mixture was then allowed to cool at room temperature. The sample was evaporated and the remaining gums/polymer weight was obtained.

The results of this testing for varying ratios of the combination of 2-aminophenol and OH-TEMPO are presented in Table I.

TABLE I

| No. | OH-TEMPO (ppm) | 2-AP (ppm) | Total (ppm) | Gums (mg/100 ml) |
|---|---|---|---|---|
| 1 | 0.75 | 0.00 | 0.75 | 34 |
| 2 | 0.56 | 0.19 | 0.75 | 37 |
| 3 | 0.50 | 0.25 | 0.75 | 33 |
| 4 | 0.375 | 0.375 | 0.75 | 55 |
| 5 | 0.25 | 0.50 | 0.75 | 59 |
| 6 | 0.19 | 0.56 | 0.75 | 56 |
| 7 | 0.00 | 0.75 | 0.75 | 78 |

Figure 2:
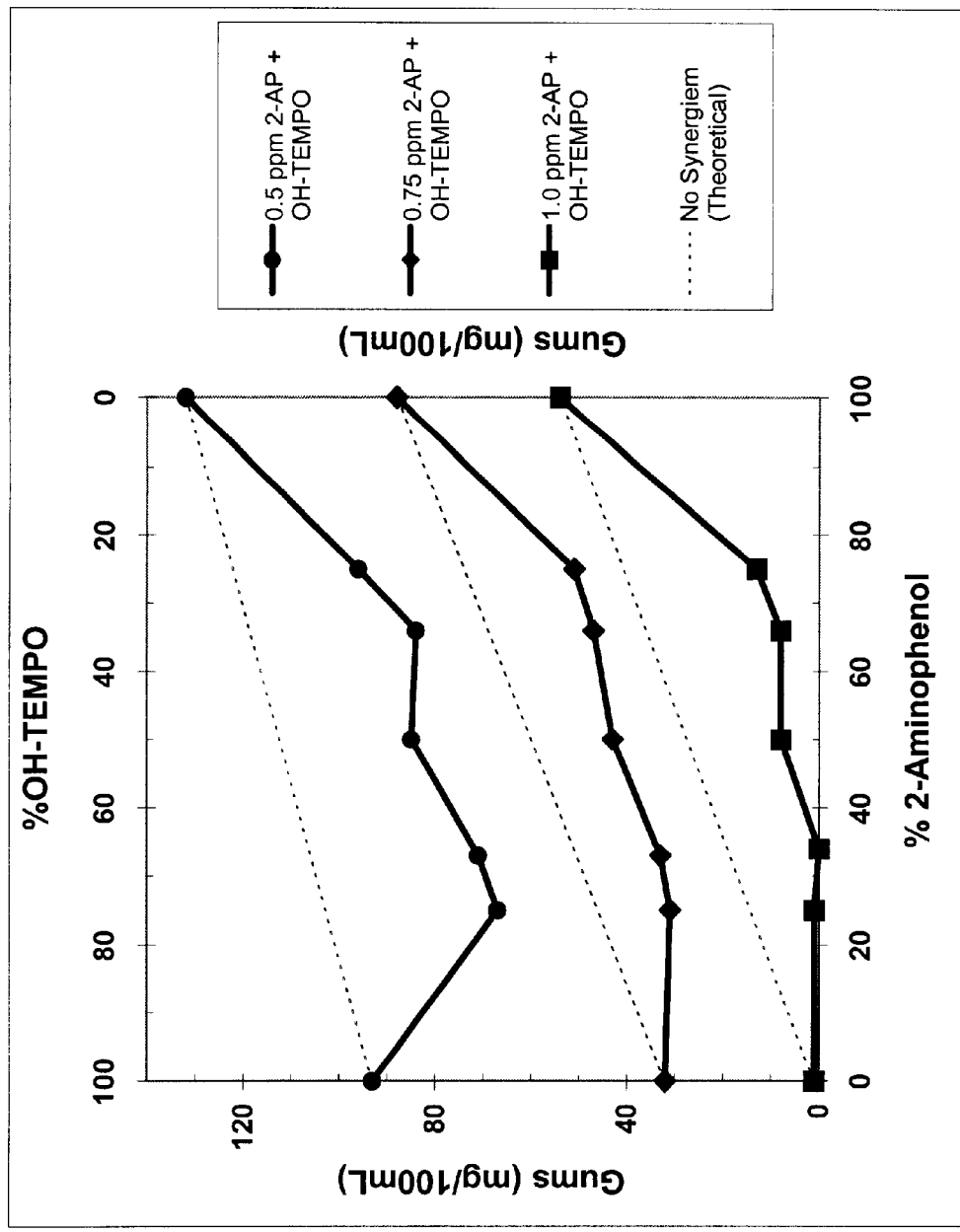
FIG. 2 is a graph of gum formation versus composition component ratio for several dosage levels as tested and reported in Tables I, IV and V below.

These results demonstrate that the combination of 2-aminophenol and OH-TEMPO is synergistic and was unexpectedly more effective than would have been predicted by a linear combination of the particular individual components (see FIG. 1 and FIG. 2).

The results of testing OH-TEMPO alone demonstrates linearity between concentration and performance as demonstrated in Table II.

TABLE II

| No. | OH-TEMPO (ppm) | 2-AP (ppm) | Total (ppm) | Gums (mg/100 ml) |
|---|---|---|---|---|
| 1 | 0.75 | 0.00 | 0.75 | 39 |
| 2 | 0.56 | 0.00 | 0.56 | 68 |
| 3 | 0.50 | 0.00 | 0.50 | 75 |
| 4 | 0.375 | 0.00 | 0.375 | 106 |
| 5 | 0.25 | 0.00 | 0.25 | 121 |
| 6 | 0.19 | 0.00 | 0.19 | 141 |
| 7 | 0.00 | 0.00 | 0.00 | 170 |

Table III presents the results of testing a combination of the non-synergistic combination of OH-TEMPO with the commercially available inhibitor BHT (2,6-di-t-butyl-4-methylphenol) at comparable concentration and ratios (see FIG. 1).

TABLE III

| No. | OH-TEMPO (ppm) | BHT (ppm) | Total (ppm) | Gums (mg/100 ml) |
|---|---|---|---|---|
| 1 | 0.75 | 0.00 | 0.75 | 31 |
| 2 | 0.56 | 0.19 | 0.75 | 77 |
| 3 | 0.50 | 0.25 | 0.75 | 84 |
| 4 | 0.375 | 0.375 | 0.75 | 102 |
| 5 | 0.25 | 0.50 | 0.75 | 112 |
| 6 | 0.19 | 0.56 | 0.75 | 121 |
| 7 | 0.00 | 0.75 | 0.75 | 156 |

Further testing was performed of total treatment of 0.5 ppm and 1 ppm are presented in Tables IV and V.

TABLE IV

| No. | OH-TEMPO (ppm) | 2-AP (ppm) | Total (ppm) | Gums (mg/100 ml) |
|---|---|---|---|---|
| 1 | 0.50 | 0.00 | 0.5 | 93 |
| 2 | 0.37 | 0.13 | 0.5 | 67 |
| 3 | 0.33 | 0.17 | 0.5 | 71 |
| 4 | 0.25 | 0.25 | 0.5 | 85 |
| 5 | 0.17 | 0.33 | 0.5 | 84 |
| 6 | 0.13 | 0.37 | 0.5 | 96 |
| 7 | 0.00 | 0.50 | 0.5 | 132 |

TABLE V

| No. | OH-TEMPO (ppm) | 2-AP (ppm) | Total (ppm) | Gums (mg/100 ml) |
|---|---|---|---|---|
| 1 | 1.00 | 0.00 | 1.0 | 1 |
| 2 | 0.75 | 0.25 | 1.0 | 1 |
| 3 | 0.66 | 0.34 | 1.0 | 0 |
| 4 | 0.50 | 0.50 | 1.0 | 8 |
| 5 | 0.34 | 0.66 | 1.0 | 8 |
| 6 | 0.25 | 0.75 | 1.0 | 13 |
| 7 | 0.00 | 1.00 | 1.0 | 54 |

Chemicals that are neither synergistic nor antagonistic will react independent of each other. Chemicals that are synergistic when mixed will perform better than what is predicted by a linear combination of individual components. This synergism will be apparent by a curvature in the line upon plotting concentration of components vs. performance. We see this effect clearly with the synergistic combination of aminophenol with the OH-TEMPO. On the other hand, the non-synergistic combination of BHT with OH-TEMPO produces a performance that is linear and predicted by a linear combination of the performance of each individual component (see FIG. 1).

The results of these tests demonstrate the enhanced activity or synergy between 2-aminophenol and OH-TEMPO at inhibiting vinyl monomer polymerization. These results also demonstrate that the combination of aminophenol with nitroxyl radical compounds is synergistic and unexpectedly more effective than would have been predicted by the linear combination of the individual components at inhibiting polymerization.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of vinyl monomers comprising adding to vinyl monomers an effective inhibiting amount of a composition comprising a combination of:

(A) at least one aminophenol compound of the formula:

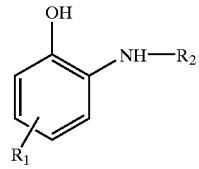

wherein $R_1$ and $R_2$ are selected from hydrogen, $C_1$–$C_{20}$ alkyl or aryl, and OR',
wherein R' is selected from hydrogen, $C_1$–$C_{20}$ alkyl, phenyl, and (B) a nitroxyl radical compound.

2. The method as claimed in claim 1 wherein said aminophenol compound is selected from 3-hydroxy-2-aminophenol, 2-amino-naphthalen--1-ol, 3-amino-naphthalen-2-ol, 1-amino-naphthalen-2-ol, 2-amino-tert-butyl-phenol, and 2-amino-4-methyl-phenol, 2-aminophenol, and 4-aminophenol.

3. The method as claimed in claim 2 wherein said aminophenol compound is 2-aminophenol.

4. The method of claim 1 wherein said nitroxyl radical compound is selected from derivatives of dialkyl nitroxyl radicals, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, bis(1-oxyl-2,2,6,6-tetramethylpiperidin-4-yl)n-butylmalonate, bis(1-oxyl-2,2,6,6-tetramethylpiperidin-4-yl)phthalate, bis(1-oxyl-2,2,6,6-tetramethylpiperidin-4-yl)isophthalate, bis(1-oxyl-2,2,6,6-tetramethylpiperidin-4-yl)terephthalate, bis(1-oxyl-2,2,6,6-tetramethylpiperidin-4-yl)hexahydroterephthalate, N,N'-bis (1-oxyl-2,2,6,6-tetramethylpiperidin-4-yl)adipamide, N-1-oxyl-2,2,6,6-tetramethylpiperidin-4-yl-dodecylsuccinimide, 1-oxyl-4-methoxy-2,2,6,6-tetramethylpiperidine, 1-oxyl-4-amino-2,2,6,6-tetramethylpiperidine and 1-oxyl-4-acetamino-2,2,6,6-tetramethylpiperidine.

5. The method as claimed in claim 4 wherein said nitroxyl radical compound is 1-oxyl-2,2,6,6-tetramethylpiperidino-4-ol.

6. The method as claimed in claim 1 wherein said aminophenol compound is 2-aminophenol and said nitroxyl radical compound is 1-oxyl-2,2,6,6-tetramethylpiperidino-4-ol.

7. The method as claimed in claim 1 wherein said vinyl monomers are selected from the group consisting of olefins and diolefins.

8. The method as claimed in claim 7 wherein said olefins and said diolefins contain about 2 to about 20 carbons.

9. The method as claimed in claim 1 wherein said composition is added to said vinyl monomers in an amount ranging from about 1 to about 10,000 parts per million parts of said hydrocarbon.

10. The method of claim 1 wherein said composition inhibits polymerization of vinyl monomers during processing.

11. The method as claimed in claim 10 wherein said processing occurs at temperatures of about 50° to about 150° C.

12. The method of claim 1 wherein said vinyl monomers are in storage conditions.

13. The method of claim 1 wherein said composition inhibits polymerization of said vinyl monomers during storage, transportation or combinations thereof.

* * * * *